United States Patent [19]

Qualeatti et al.

[11] Patent Number: 4,524,225
[45] Date of Patent: Jun. 18, 1985

[54] ACID RESISTANT CATALYST SUPPORTS; REDUCTION OF FATTY ACIDS TO FATTY ALCOHOLS

[75] Inventors: Gail M. Qualeatti, Palatine; Bruce I. Rosen, Skokie; Blaise J. Arena; Dalia Germanas, both of Des Plaines, all of Ill.

[73] Assignee: UOP Inc., Des Plaines, Ill.

[21] Appl. No.: 561,491

[22] Filed: Dec. 14, 1983

[51] Int. Cl.³ ............................................. C07C 27/04
[52] U.S. Cl. ..................................... 568/885; 568/884
[58] Field of Search ........................ 568/659, 884, 885

[56] References Cited

U.S. PATENT DOCUMENTS 3,729,520  4/1973  Rutzen et al. ...................... 568/885
4,446,073  5/1984  Qualeatti et al. ................... 568/885

FOREIGN PATENT DOCUMENTS 712197   6/1965   Canada ................................. 568/885
3217429  12/1982  Fed. Rep. of Germany ...... 568/885

Primary Examiner—Werren B. Lone
Attorney, Agent, or Firm—William H. Page, II; Eugene I. Snyder

[57] ABSTRACT

Several materials, suitable as carriers or supports for zerovalent metals dispersed thereon have been found to be appreciably more corrosion resistant in the environment of organic acids than are conventional supports, among which are included alpha-alumina, theta-alumina, titanated alumina, titania, and aluminum phosphate. The discovery of such corrosion resistant supports permits a continuous process for the hydrogenation of a fatty acid to its fatty alcohol using a fixed catalyst bed of a zerovalent metal dispersed on a carrier of this invention.

8 Claims, No Drawings

ACID RESISTANT CATALYST SUPPORTS; REDUCTION OF FATTY ACIDS TO FATTY ALCOHOLS

BACKGROUND OF THE INVENTION

Many transformations of organic compounds are catalytic processes mediated by metals. In such catalytic transformations, which include alkylation, ammination, oxidation, hydroformylation, and reduction, as a general proposition the metal is not utilized per se but is instead supported on an inert carrier to gain the benefits of increased dispersion. A characteristic of many common supported catalysts used with organic acid feedstocks is that the supported metal and the underlying carrier tend to leach into the liquid phase under reaction conditions. Using nickel on gamma-alumina as an example of a supported catalyst, in the presence of a highly corrosive feedstock of an organic acid both nickel and alumina tend to dissolve.

A disadvantage of such prior art catalysts is that the product contains relatively high levels of metal as a contaminant. Such a product may have considerably reduced commercial value because of the metal contamination, or may require relatively costly processing to remove such contamination before affording a commercially acceptable material.

Another disadvantage of such supports is their limited use in continuous processes. For example, where a fixed bed continuous process is desired it is clearly mandatory that the bed retain its physical integrity. But it follows just as clearly that such integrity is impossible where the carrier dissolves in the feedstock. Thus, many catalyst transformations of organic acids are presently unfeasible in a continuous mode because commonly used supports are structurally inadequate.

Still another disadvantage of prior art supports is that their tendency to leach makes subsequent catalyst regeneration difficult if not impossible. For example, leaching may cause a sufficient change in composition as to make regeneration impractical. It will be recognized that regeneration of a catalyst is highly desirable.

The limitations of prior art catalysts spurred our search for carriers, or supports, which would be sufficiently inert in the corrosive atmosphere of organic fatty acids as feedstocks, or as substantial components of feedstocks, to overcome the aforementioned disadvantages. In particular, we sought carriers whose levels of leaching are sufficiently low as to permit their use in a continuous, fixed bed process. We have discovered several carriers whose corrosion resistance in the presence of fatty acids makes possible a continuous, fixed bed process utilizing as a catalyst a metal(s) supported on these carriers.

SUMMARY OF THE INVENTION

An object of this invention is to provide supported catalysts whose resistance to the corrosive nature of fatty acids permits their use in a continuous catalytic transformation of a feedstock containing a fatty acid. In one embodiment the support is alpha-alumina, theta-alumina, titanated alumina, titania, aluminum phosphate, or combinations thereof. In another embodiment the catalytic transformation is hydrogenation. In a still more specific embodiment, the hydrogenation catalyst is a metal selected from the group consisting of copper, chromium, ruthenium, platinum, palladium, rhenium, and combinations thereof dispersed on said supports.

DESCRIPTION OF THE INVENTION

In its broad aspect the invention herein is an improvement in any catalytic transformation of an organic acid, or of a feedstock containing a substantial amount of an organic acid, using a metal dispersed on a support, the improvement being a corrosion resistant support selected from the group consisting of alpha-alumina, theta-alumina, titanated alumina, titania, aluminum phosphate, and combinations thereof. In its narrower aspect the invention is a method of hydrogenating a fatty acid, or a mixture of the acid and its ester, to a fatty alcohol comprising contacting the fatty acid or the aforesaid mixture with hydrogen under hydrogenation conditions in the presence of a zerovalent metal selected from the group consisting of copper, chromium, ruthenium, platinum, palladium, rhenium, and combinations thereof dispersed on one of the aforementioned supports and recovering the fatty alcohol produced thereby. Both aspects of our invention are based on our discovery that certain materials suitable for use as carriers, or supports, for catalytically active metals dispersed thereon are particularly stable in the highly corrosive environment of an organic acid. The supports of our invention are atypical, that is, they are not conventional materials for supported catalysts. Our supports are uniquely valuable because catalysts comprising a metal dispersed on the supports described herein are particularly resistant to the corrosive environment of a fatty acid, hence may be successfully used in a continuous fixed bed process, which stands in stark contrast to more conventional supports.

By catalytic transformation is meant any catalytic process using an organic acid as a reactant. Among the more commonly employed catalytic transformations, cited for illustrative purposes only and which are by no means exhaustive, are included alkylation, ammination, oxidation, hydroformylation, and reduction.

The corrosive nature of an organic acid is equated with its pH. The broadest class of organic acids are those containing the carboxyl group, $CO_2H$. Therefore, the most common group of organic materials to which our invention pertains consists of organic carboxylic acids. However, other materials, especially phenols, occasionally exhibit an acidity typical of carboxylic acids. It is to be understood that the invention herein may be used with any organic material with an acidity in the range of organic carboxylic acids.

The catalytic transformations of this invention generally are mediated by metals which usually are dispersed on a carrier, or support, so as to increase the effective surface area which the metal presents while maintaining heterogeneity and particle size conducive to ease of handling. Among the metals which are so employed are included cadmium, indium, tin, antimony, tungsten, rhenium, osmium, iridium, platinum, gold, mercury, lead, vanadium, chromium, manganese, iron, cobalt, nickel, copper, zinc, molybdenum, ruthenium, rhodium, palladium, and silver.

The supports, or carriers, of our invention are corrosion resistant materials, that is, materials whose dissolution in the corrosive environment of an organic acid is substantially less than conventional supports. A standard test consists of contacting one gram of support with 25 grams of octanoic acid at 150° C. and 200 atmospheres hydrogen for 12 hours, then analyzing the filtrate for dissolved metal. For a conventional support such as gamma alumina it is found that the filtrate contains about 2 percent, or 20,000 ppm, aluminum. In the supports of this invention the extent of dissolution is never more than about 0.7 percent, usually is under 0.3 percent, and is more typically under about 200 (0.02%) ppm. Thus it can be seen that the supports herein are considerably more corrosion resistant than prior art materials. Among the supports are alpha alumina, theta-alumina, titanated alumina, titania, and aluminum phosphate. It is to be understood that by alpha-alumina is meant alumina whose crystallinity as measured by X-ray diffraction corresponds to that characterized in ASTM file #10-173. By theta-alumina is meant alumina whose crystallinity as measured by X-ray diffraction corresponds to that characterized in the Joint Committee on Powder Diffraction Standards #23-1009. By titanated alumina is meant an alumina prepared by treating alumina with a titanium tetrahalide under conditions where the titanium-halogen bond is not hydrolyzed, removing adhering but unreacted excess $TiX_4$, then oxidizing the material obtained thereby at a temperature from about 100° C. to about 500° C. The resulting material can thereafter be steam treated to remove halide ion. Titanium tetrachloride is the tetrahalide of choice, although the bromide or fluoride may be used, but not necessarily with equivalent results.

A particularly important aspect of this invention is the catalytic hydrogenation of a fatty acid to a fatty alcohol. Because fatty acid esters sometimes are more available, or more convenient to work with, than are fatty acids, reduction of fatty acid esters is an alternate route to production of fatty alcohols. But when fatty acid esters are used as the feedstock in reduction the presence of fatty acids must be reduced to less than about 2% because of their corrosive effects. Hence, our process is directed toward reduction of feedstocks of a fatty acid, or a fatty ester containing more than about 2% by weight, relative to all esters, of free fatty acids.

By a fatty acid is meant a linear, unbranched carboxylic acid containing from about 6 to about 24 carbon atoms. Acids containing from 10 to about 18 carbon atoms are especially important, and within this group those carboxylic acids containing an even number of carbon atoms are particularly important. The fatty acids of this invention may be either saturated or unsaturated. Examples of suitable fatty acids include hexanoic acid, heptanoic acid, octanoic acid, nonanoic acid, decanoic acid, undecanoic acid, dodecanoic (lauric) acid, tridecanoic acid, tetradecanoic (myristic) acid, pentadecanoic acid, hexadecanoic (palmitic) acid, heptadecanoic acid, octadecanoic (stearic) acid, nonadecanoic acid, eicosanoic acid, oleic acid, linoleic acid, linolenic acid, erucic acid, and so on. By a fatty acid ester is meant any alkyl ester of a fatty acid, the nature of the alkyl group being unimportant. Examples of some of the more commonly employed alkyl groups include methyl, ethyl, glyceryl, and the higher linear alkyl groups containing from about 12 to about 20 carbon atoms.

In hydrogenation the fatty acid or ester is converted to the fatty alcohol, that is, the carboxyl group, $CO_2H$, or carboalkoxy group, $CO_2R$, is converted to the hydroxymethyl group, $CH_2OH$. This conversion may be accompanied by reduction of a carbon-carbon double bond if the latter is originally present in the fatty acid used.

Among the zerovalent metals which may be used in the practice of this invention are included copper, chromium, ruthenium, platinum, palladium, rhenium, and combination thereof. The amount of metal used depends, inter alia, upon reaction conditions and the particular metal or metal combination employed. For example, where ruthenium is used levels of metal based on fatty acid present range from about 0.01 to about 0.5 wt. percent.

The fatty acid or fatty acid ester containing more than about 2% fatty acids is contacted with a zerovalent metal dispersed on one of the corrosion resistant supports discussed previously. Where the surface area of the corrosion resistant support is relatively low, there is present a relatively low loading of zerovalent metal, typically on the order of about 0.1 to about 5 percent. Where the surface area is greater, approaching that of a conventional support, higher loadings, up to about 20 percent, may be possible, although even with high surface area supports the quest for high dispersion of metal generally keeps loading below about 10 percent. The fatty acid is contacted with the supported metal and hydrogen under hydrogenation conditions. The latter include a hydrogen pressure from about 100 to about 3,000 psig with the range from about 500 to 2,000 psig being preferred. Hydrogenation conditions also employ a temperature from about 100° to about 300° C., more usually from about 150° to about 275° C., with a still more preferred range from about 200° to about 250° C.

Hydrogenation of a fatty acid or ester to its fatty alcohol according to the invention herein may be performed either in a batch or a continuous process. A continuous process is particularly favored, for it is here where the advantage of our corrosion resistant catalyst may be maximally enjoyed. Among the continuous modes a fixed bed process is favored, in part for its simplicity. In this process a zerovalent metal selected from the group consisting of copper, chromium, ruthenium, platinum, palladium, rhenium, or combinations thereof dispersed on a support of alpha-alumina, theta-alumina, titanated alumina, titania, aluminum phosphate, or combinations thereof, is used as a fixed catalyst bed. A fatty acid or ester in liquid form is then passed through this bed in the presence of hydrogen and a pressure from about 100 to 3,000 psig and at a temperature between about 100° and 300° C. The liquid hourly space velocity of the feedstock is controlled so as to effect optimum conversion of the fatty acid to the fatty alcohol. The fatty alcohol produced in the hydrogenation is then collected as the effluent.

The examples given below are merely illustrative of this invention and are not intended to limit it in any way.

EXAMPLE 1

A series of supports and of metals dispersed thereon were prepared to test their corrosion resistance in the environment of an organic acid. Material A is a one percent zerovalent ruthenium on gamma alumina prepared by impregnating an alumina of surface area 200 $m^2/g$, micropore volume 0.5 ml/g and macropore volume 0.3 ml/g, with an aqueous solution of ruthenium trichloride by steam evaporation. The impregnate subsequently was calcined in air at 450° C. for two hours then reduced in hydrogen at 450° C. for three hours. Material B is a one percent ruthenium dispersed on theta-alumina, the latter prepared from the aforementioned gamma alumina by calcination at 1100° C. The theta-alumina was impregnated with aqueous ruthenium trichloride with subsequent steam evaporation, the impregnate then being reduced in hydrogen at 400° C. for three hours. Material C was a theta alumina prepared by calcining a gamma alumina whose properties include a surface area of 169 m²/g and a total pore volume of 1.67 cc/g at 1000° C. for three hours. Preparation D was one percent ruthenium dispersed on alpha-alumina prepared from the gamma alumina described in A by calcination at 1650° C. Impregnation was carried out as described previously. The resultant impregnate was calcined in air at 450° C. for two hours and reduced in hydrogen at 450° C. for three hours. E was a one percent rhenium - 0.1 percent platinum on the aforementioned alpha alumina prepared by impregnation with ammonia perrhennate (NH$_4$ReO$_4$) and chloroplatinic acid using steam evaporation. The resulting impregnate was calcined in air for two hours at 500° C. and reduced in hydrogen for 1.5 hours at 500° C. Material F was an alpha-alumina prepared from a gamma-alumina, with properties which include a surface area of 160 m²/g and a total pore volume of 1.77 cc/g, by calcining the latter at 1100° C. for 20 hours. Material G was one percent ruthenium dispersed on titanated alumina. A titanated alumina was impregnated with aqeuous ruthenium chloride by steam evaporation. The impregnate was reduced in hydrogen for three hours at 250° C. Sample H was one percent zerovalent ruthenium dispersed on titania prepared by steam evaporation of an aqueous solution of ruthenium chloride on titania powder subsequently reduced with hydrogen at 220° C. for three hours. Aluminum phosphate, material I, was an oil dropped sphere prepared in the following manner. Concentrated phosphoric acid was added in an amount sufficient to give a Al/P atomic ratio of 0.94 to an aluminum chloride hydrosol (Al/Cl=0.88 atomic ratio). Hexamethylenetetramine was added as a settling agent and the mass was dropped into hot forming oil. The spheres were pressure aged at 140° C. for 1.5 hours, then water washed, dried, and calcined at 550° C.

EXAMPLE 2

All materials were screened using a standard stability test. A mixture of octanoic acid (25 g) and the material to be tested (1.0 g) were charged to an 850 cc glass autoclave liner. The liner was loaded into a rotating autoclave, pressured to 200 atmospheres with hydrogen, and heated to 150° C. After 12 hours at the latter temperature, the reactor was cooled and the material was filtered through a 0.45 micron millipore filter. The filtrate was then analyzed by atomic adsorption spectroscopy for the metal(s) of the support and any metal dispersed thereon. The extent of aluminum dissolution was found to be independent of the presence or absence of a metal dispersed thereon, independent of the nature of the dispersed metal, if any, and also was independent of the source of alumina. Results are tabulated below.

| STABILITY OF MATERIALS TOWARD LEACHING | | |
|---|---|---|
| Material | Leached Metal | Leached Support |
| A. | Less than 1.5 ppm Ru | 2.0 wt % Al |
| B. | Less than 1.5 ppm Ru | 0.23 wt % Al |
| C. | | 0.28 wt % Al |
| D. | 1.9 ppm Ru | 6.3 ppm Al |
| E. | | 5.3 ppm Al |

| -continued | | |
|---|---|---|
| STABILITY OF MATERIALS TOWARD LEACHING | | |
| Material | Leached Metal | Leached Support |
| F. | | 19 ppm Al |
| G. | 4.2 ppm Ru | 100 ppm Ti |
| | | 0.72 wt. % Al |
| H. | 1.5 ppm Ru | 0.9 ppm Ti |
| I. | | 162 ppm Al |

EXAMPLE 3

A 300 ml stirred autoclave was charged with a fatty acid and catalyst under nitrogen, sealed, and pressurized to 1000 psig with hydrogen. The reactor was brought to temperature, hydrogen pressure was adjusted to and maintained at 1500 psig, and the mixture stirred at 1200 rpm until hydrogen uptake ceased. The reaction mixture then was cooled to room temperature and analyzed by gas liquid phase chromatography. Some results are summarized in the accompanying table.

| Feedstock | Lauric Acid | Decanoic Acid |
|---|---|---|
| Wt. (gms) | 100 | 100 |
| Catalyst | 1% Re/AlPO$_4$ | 3% Ru/α-Al$_2$O$_3$ |
| Wt. (gms) | 5 | 10 |
| Temperature (°C.) | 240 | 240 |
| P (psig) | 120 | 130 |
| Time (min.) | 415 | 350 |
| GC Analysis | | |
| C$_{10}$ Alcohol | | 6.4 |
| C$_{10}$ Acid | | 27.7 |
| C$_{12}$ Alcohol | 15.4 | |
| C$_{12}$ Acid | 10.1 | |
| C$_{10}$—C$_{10}$ Ester | | 54.9 |
| C$_{12}$—C$_{12}$ Ester | 71.0 | |
| Others | 3.5 | 11.0 |

As the table shows, most of the reduction product shows up as the ester of the formed fatty alcohol and reactant fatty acid.

What is claimed is:

1. A method of hydrogenating a fatty acid containing from about 6 to about 24 carbon atoms, or an ester thereof containing more than about 2% free fatty acids, to a fatty alcohol comprising contacting said acid or ester with hydrogen at a temperature from about 100° to about 300° C. and a pressure from about 100 to about 3000 psig in the presence of a zerovalent metal selected from the group consisting of copper, chromium, ruthenium, platinum, palladium, rhenium and combinations thereof dispersed on a support of alpha-alumina, theta-alumina, titanated alumina, titania, or aluminum phosphate, or combinations thereof, and recovering the fatty alcohol produced thereby.

2. The method of claim 1 where the fatty acid contains from 10 to about 18 carbon atoms.

3. The method of claim 2 where the fatty acid contains an even number of carbon atoms.

4. The method of claim 1 where the metal is ruthenium.

5. The method of claim 1 where the metal is rhenium.

6. The method of claim 1 where the pressure is from about 500 to about 2,000 psig.

7. The method of claim 1 where the temperature is from about 150° to about 275° C.

8. The method of claim 7 where the temperature is from about 200° to about 250° C.

* * * * *